United States Patent [19]
Metz et al.

[11] Patent Number: 4,889,532
[45] Date of Patent: Dec. 26, 1989

[54] FEMALE URINARY INCONTINENCE DEVICE WITH FORWARDLY-DIRECTED DISCHARGE PASSAGE AND SUPPORT SURFACE PORTIONS

[75] Inventors: Michael Metz, Chicago; Joseph S. Tokarz, Palatine; Marvin E. Jensen, Niles, all of Ill.

[73] Assignee: Hollister Incorporated, Libertyville, Ill.

[21] Appl. No.: 209,541

[22] Filed: Jun. 21, 1988

[51] Int. Cl.$^4$ ............................................. A61F 5/44
[52] U.S. Cl. .................................... 604/330; 4/144.3; 128/761
[58] Field of Search ................................ 604/329–330, 604/331, 329–331; 128/760, 761, DIG. 21, 774, 775, 760, 761, 774, 775; 4/144.1–144.4

[56] References Cited

U.S. PATENT DOCUMENTS

| | | |
|---|---|---|
| 3,194,238 | 7/1965 | Breece, Jr. |
| 4,194,508 | 3/1980 | Anderson ............................ 604/329 |
| 4,681,572 | 7/1987 | Tokarz et al. ......................... 604/329 |

Primary Examiner—Jerome L. Kruter
Attorney, Agent, or Firm—Tilton, Fallon, Lungmus

[57] ABSTRACT

A female urinary incontinence device including a periurethral cup, an external pad of soft, flexible, resilient material, and a compressible tubular elastic bellows extending between a lower opening of the cup and the inlet to a fluid discharge passage extending through the pad. The discharge passage extends forwardly (anteriorly) in a generally horizontal direction along the sagittal midplane of the pad, and the undersurface of the pad is provided with laterally-disposed and generally-horizontal surface portions, and preferably also a coplanar medial surface portion, for distributing forces and preventing inversion of the pad when a wearer is seated. A flexible discharge tube has one end detachably connected to the pad's discharge passage by means of a tubular coupling having an insert portion received in the outlet of that passage. The coupling includes a laterally-directed vent and valve, and an upwardly-extending T-shaped (in section) projection of the coupling is frictionally received in a T-shaped slot in the pad for preventing rotation of the coupling with respect to the pad and for holding the coupling in alignment, and in flow communication, with the pad's discharge passage.

17 Claims, 3 Drawing Sheets

FEMALE URINARY INCONTINENCE DEVICE WITH FORWARDLY-DIRECTED DISCHARGE PASSAGE AND SUPPORT SURFACE PORTIONS

BACKGROUND

Various devices have been proposed for directing and collecting urine from female patients suffering from urinary incontinence. One such device, believed to be particularly effective in adapting to the varied and complex anatomical changes that occur in the periurethral area during locomotion, is disclosed in co-owned U.S. Pat. No. 4,681,572. In that construction, a periurethral cup and an external pad, both formed of soft, compressible material, are connected together by means of a tubular elastic bellows that exerts an upward force on the cup when the device is worn while, at the same time, permitting limited independent movement of the cup and pad. In use of the device, the external pad is held upwardly against the external surfaces of the labia majora by a panty or other support means and the periurethral cup projects upwardly inside the labia majora and minora and is positioned so that its soft rounded upper surfaces engage the periurethral floor about the urethral meatus. The partially compressed elastic bellows exerts a constant gentle upward force on the cup to maintain the cup in proper position and, because of its construction and elasticity, the bellows is capable of twisting, bending, and deflecting to accommodate the dynamics of body movement.

The effectiveness of the device of the aforementioned patent therefore results in part from the fact that the elastic bellows is partially compressed when worn by a patient. To achieve such partial compression for patients of different size, the patent discloses a sizing instrument (FIG. 7) that may be conveniently used for establishing the bellows length for any given patient.

The construction disclosed in the patent makes it possible for wearers suffering from urinary incontinence to partake in many of the same ambulatory activities enjoyed by those who are not so afflicted. Such freedom brings problems, however, and it is the recognition of such problems, and the improvements in construction that eliminate or reduce them, to which this invention is directed.

Other patents revealing the development of the art with respect to female urinary incontinence devices include U.S. Pat. Nos. 4,496,355, 4,421,511, 4,270,539, 4,246,901, 4,198,979, 4,194,508, 3,995,329, 3,776,325, 3,661,155, 3,528,423, 3,512,185, 3,194,238, 3,116,734, 2,490,969, and 2,483,079.

SUMMARY OF THE INVENTION

It has been discovered that because of the wide range of body movements permitted by the device of U.S. Pat. No. 4,681,572 without causing disengagement or leakage, situations might arise where some patient discomfort could possibly occur. For example, when a patient is in seated position, upward force on external pad 12, 212 might cause substantially full compression of the bellows 13, 213. Should reversal of curvature of the deformable external pad 12, 212 also occur, the force transmitted by the cup 11, 211, fully-collapsed bellows 13, 213, and inverted pad 12, 212 might well produce wearer discomfort. Also, drainage tube 14, 214 may become kinked when the wearer is seated, thereby interfering with proper operation of the device. Should a wearer shift in position while seated, forces exerted against or transmitted by such a drain tube might be sufficient to cause uncoupling of the tube from the remainder of the device.

Tube-uncoupling problems might be dealt with by providing a construction in which a drainage tube and external pad are permanently connected, but such a construction would then present additional problems. The optimum length for a drainage tube varies not only according to the patient's physical dimensions but also with the type of clothing or mode of dress selected by the wearer. It thus becomes important for a wearer to be able to join drainage tubes of different selected lengths to a given pad-bellows-cup assembly, and to do so in a way that gives assurance the parts are in fact properly coupled together and will not become inadvertently disconnected in use.

One aspect of the present invention lies in providing a female urinary incontinence device that achieves the advantages of the device of U.S. Pat. No. 4,681,572 but in which the fluid discharge passage of the external pad extends forwardly (anteriorly) in a generally horizontal direction along the sagittal midplane of the pad. Although the pad has a concave upper surface to fit comfortably against the external surfaces of the labia majora, the undersurface of the pad is provided with a pair of laterally-disposed horizontal surface portions, and preferably a co-planar medial surface portion, that distribute forces and prevent inversion of the pad when a wearer is seated.

A flexible discharge tube has one end detachably connected to the external pad's discharge passage by means of a tubular coupling having an insert portion received in the outlet of that passage. Despite the softness and deformability of the pad, forces exerted on the discharge tube during normal use do not allow the portion of the pad defining the outlet of the discharge passage (which functions as a socket to receive the coupling) to flex away from the remainder of the pad. A T-shaped projection of the coupling is frictionally received in a T-shaped slot in the pad to insure that forces tending to urge the coupling downwardly or laterally will also cause similar deformations in the anterior portion of the pad. Detachment of the coupling from the pad is therefore effectively resisted because the pad's socket-providing portion and the anterior portion directly thereabove flex or deform together.

A laterally-directed vent and one-way valve are provided in the detachable coupling and, therefore, replacement of the valve (by replacing the coupling) may be readily achieved. Because the vent faces laterally, the chances of that vent becoming obstructed during normal use of the device are extremely unlikely.

Other features, advantages and objects will appear from the specification and drawings.

DRAWINGS

DETAILED DESCRIPTION OF PREFERRED EMBODIMENT

Figure 1:
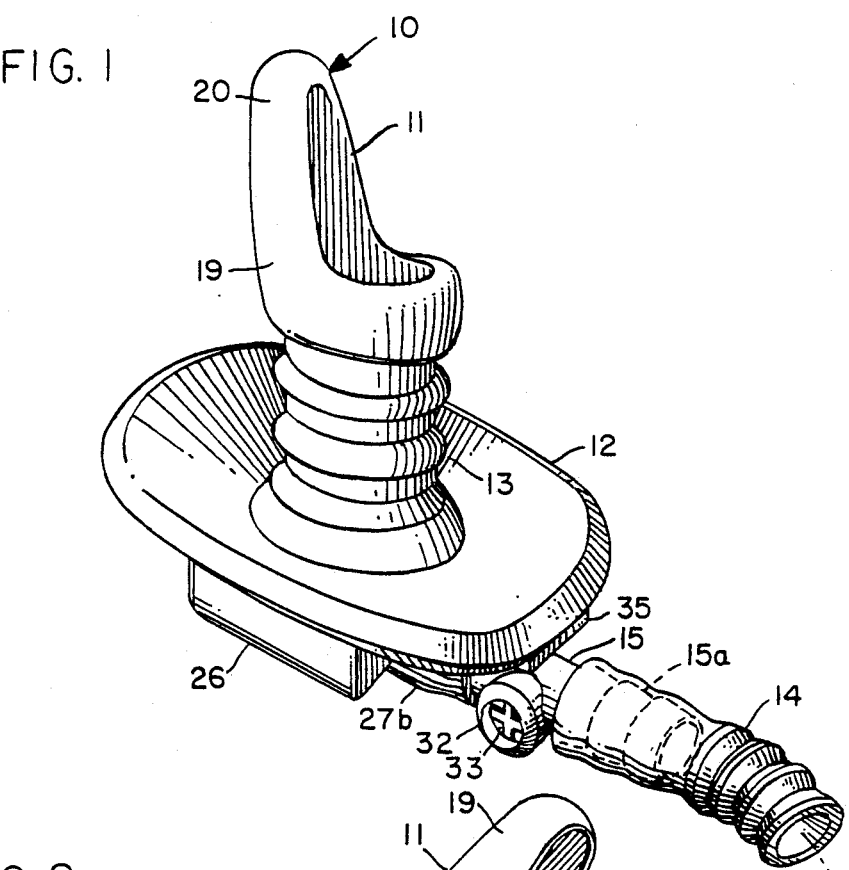
FIG. 1 is a perspective view of a female urinary incontinence device embodying this invention, with certain elements of the complete system being depicted schematically.
Figure 2:
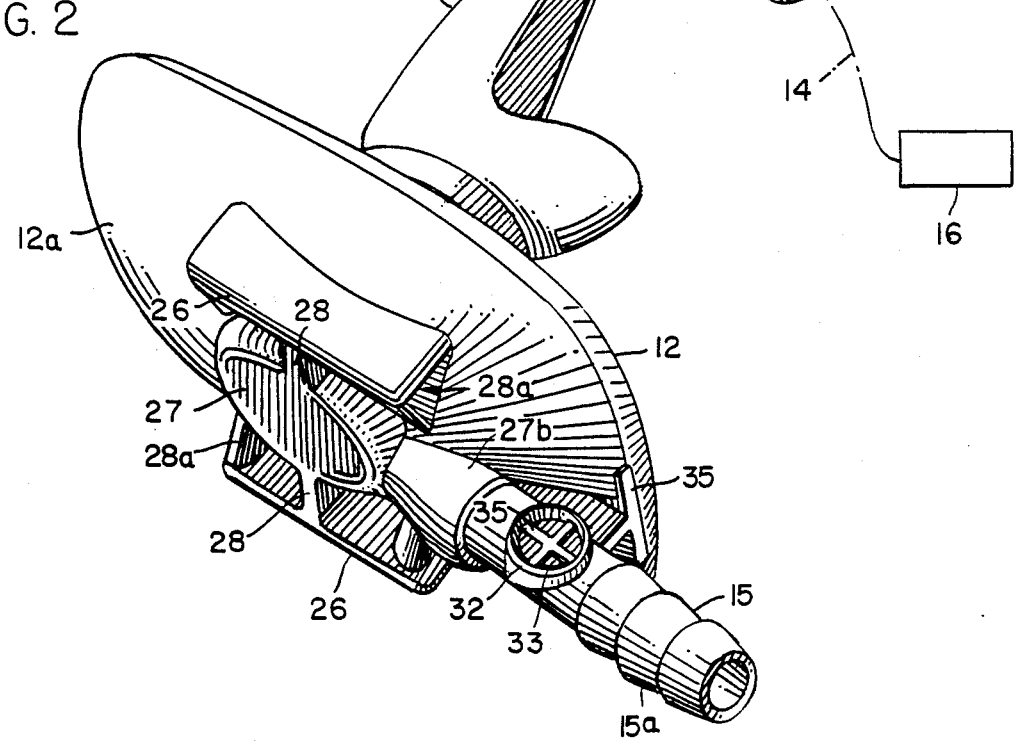
FIG. 2 is a perspective view of the underside of the device.

Referring to the drawings, numeral 10 generally designates a female urinary incontinence device comprising a periurethral cup 11, an external pad 12, a tubular elastic bellows 13, and a flexible drainage tube 14 equipped at one end with a tubular coupling 15. The opposite end of the drainage tube 14 is connected to a collector 16 which may take the form of a leg bag of the type disclosed in U.S. Pat. No. 4,681,572. It is to be understood, however, that other types of collectors might be provided to suit a patient's needs and preferences.

The periurethral cup 11 and bellows 13 are preferably molded in one piece from a soft, compressible, and form-recovering material. A molded elastomeric silicone material having a smooth, substantially non-porous outer surface has been found particularly effective, but other molded compressible materials, such as elastomeric foam materials, might be used. Reference may be had to the aforementioned patent for a discussion of such materials.

Figure 5:
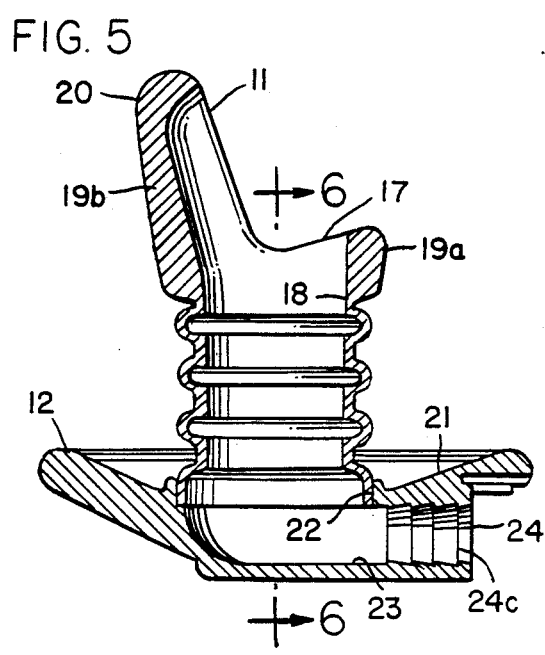
FIG. 5 is a sagittal sectional view taken along line 5—5 of FIG. 4.
Figure 6:
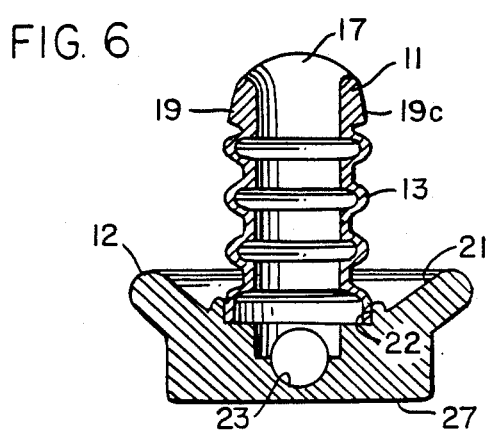
FIG. 6 is a transverse sectional view taken along line 6—6 of FIG. 5.

The side wall of the periurethral cup has substantial thickness and its uppermost surfaces are smoothly curved or rounded as shown clearly in FIGS. 5 and 6. More specifically, the cup has upper and lower openings 17 and 18, respectively. The integral side wall 19 of the cup is composed of front, rear, and lateral wall portions 19a, 19b, and 19c, respectively. In the region bordering top opening 17, each of those wall portions should have a thickness within the range of about 3 to 15 millimeters, resulting in a cup which has smoothly-rounded upper surfaces for making substantial contact with the periurethral floor and vaginal introitus.

The rear portion 19b curves upwardly beyond the upper limits of the front and lateral wall portions to define a resilient, vaginally-insertable, urine deflecting extension or protuberance 20. The essential purpose of the protuberance is to serve as a urine deflector for that portion of the female population, estimated at between 15 to 20%, whose urethral orifice is located within, or immediately adjacent, the vaginal introitus. Any functions the protuberance performs in locating and retaining the cup in position are of secondary significance.

External pad 12 should be formed of soft, compressible form-recovering material that may be the same polymeric material selected for periurethral cup 11 and bellows 13. The pad is generally oval in outline, substantially larger than cup 11, and has a concave upper surface defining a recess 21. At the center of the recess is an upwardly-facing inlet 22 located at one end of a generally horizontal fluid discharge passage 23. It will be observed that the discharge passage 23 extends along the sagittal midplane of the external pad 12 and of the device as a whole. The passage extends forwardly or anteriorly from inlet 22 to outlet 24 disposed beneath the forward rim of the pad.

The cup 11, pad 12, and bellows 13 may be formed integrally or as separate components that are permanently joined together in a final stage of manufacture. It has been found particularly convenient to form the cup and bellows as an integral unit and then secure the lower end of the bellows to the external pad at inlet 22 by means of any suitable adhesive or solvent. Such a construction is also advantageous because it allows external pads of identical construction to be joined to cup/bellows units having bellows of different lengths. As already indicated, and as fully described in U.S. Pat. No. 4,681,572, it is important that to properly fit a user, such a device should have a bellows length that will insure partial compression of the bellows when the device is worn under normal conditions of use.

The undersurface 12a of the pad has a generally convex curvature and is provided with a pair of integral, horizontally-elongated, support surface portions 26 spaced along opposite sides of the sagittal midplane of the pad. The pad also includes a medial support surface portion 27 which merges with the forwardly-extending neck portion 12b of the pad that defines outlet 24. Neck portion 27b is therefore a forward extension of medial support surface portion 27. Integral reinforcing webs 28 may interconnect the parallel side support surface portions 26 with medial support surface portion 27 and, in addition, triangular reinforcing or bracing gussets 28a may extend from the ends of each portion 26 to the convex undersurface 12a of the pad. Of particular importance is the fact that the side and medial portions 26 and 27 all have undersurfaces that lie along the sam plane which extends generally horizontally when the device is in a position of use as depicted in FIGS. 1 and 4–6.

The support surface portions, and particularly the laterally-disposed support surface portions 26, operate to distribute forces and prevent inversion of the pad when a wearer is seated. If the laterally-disposed surface portions 26 were omitted, upward forces exerted against only the medial portion 27 of the pad when a wearer is seated would tend to invert or reverse the shape of the pad, diminishing or eliminating recess 21 and fully compressing bellows 13. It is believed apparent that any substantial upward force transmitted by fully-collapsed bellows 13 and cup 11 against the periurethral floor and vaginal introitus might cause substantial wearer discomfort. Such inversion is prevented primarily by the side support surface portions 26. Also, because of the substantial forward-rearward longitudinal extent of the side portions 26 and the extension of the medial portion 27 and neck 27b well in front of those side portions, such portions produce a stabilizing effect and reduce the possibility that the pad might tip or twist away from the labia majora when a patient shifts in a seated position. Since the undersurfaces of portions 26 and 27 are below outlet 24, and since the outlet faces forwardly rather than downwardly, deformation of the pad when a wearer is seated, if it occurs to any appreciable extent, would not be expected to significantly constrict fluid discharge passage 23.

The discharge tube 14 may be formed of silicone rubber or any other suitable elastomeric material and, as shown in FIG. 1, may be corrugated or convoluted to facilitate flexing and reduce the possibilities of kinking. One end of the tube (its proximal end) is secured to the distal end 15a of tubular coupling 15. The coupling may be formed of nylon or any other tough and relatively rigid plastic material having similar properties. The proximal insert portion 15b of the coupling is tightly received in the outlet or socket 24 of pad 12. Secure interconnection between the parts may be enhanced by providing the coupling with annular shoulders 15c, and the inner surface of the outlet with mating shoulders 24c (FIG. 5) so that such shoulders effectively operate as barbs to lock the parts together.

Figure 7:
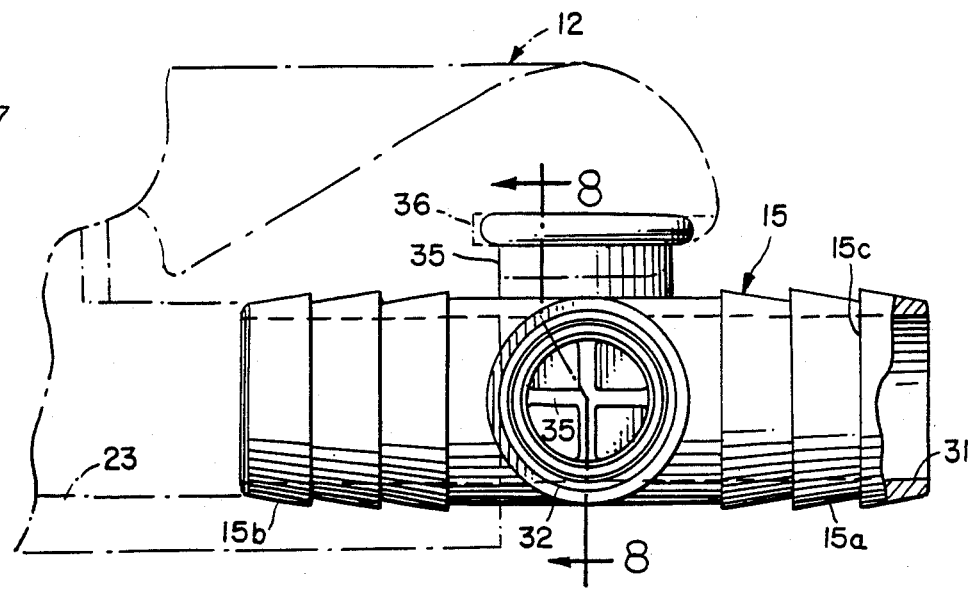
FIG. 7 is an enlarged side elevational view of the coupling, shown partly in section, with portions of the external pad depicted in phantom.
Figure 8A:
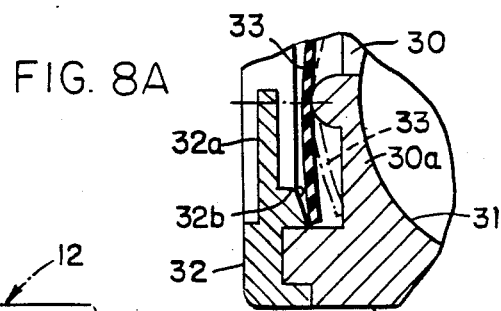
FIG. 8A is an enlarged view of a portion of FIG. 8 showing the operation of the flexible valve member.
Figure 8:
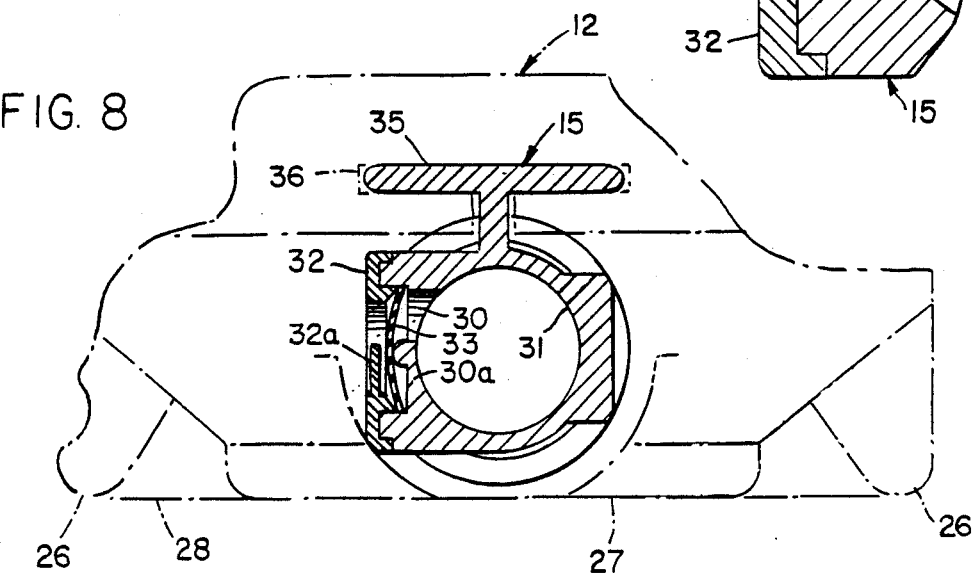
FIG. 8 is a cross sectional view taken along line 8—8 of FIG. 7.

A laterally-facing vent 30 is provided in the wall of tubular coupling 15 and communicates with the longitudinal passage 31 of that coupling (FIG. 8). An apertured cap 32 is secured to the coupling about the periphery of vent 30 by a suitable adhesive or by heat or solvent sealing and, as indicated in FIGS. 7 and 8, both the cap and the coupling are provided with radially-extending ribs 32a and 30a, respectively, for retaining a flexible valve disc or member 33 there between. The disc may be formed of silicone rubber or any other impervious elastomeric material. The disc is planar in an unflexed or undeformed state; however, when disposed in operative position between the ribs 32a and 30a of the cap and coupling, the disc assumes a slightly concavo-convex shape with its convex surface facing outwardly towards cap 32. An annular edge 32b of the cap sealingly engages the convex periphery of the disc to prevent leakage of fluids from coupling 15. However, should the pressure within the passage 31 of the coupling drop a predetermined extent below ambient pressure (for example, 0.5 inches H2O), the periphery of the disc flexes inwardly into the position depicted in broken lines (FIG. 8A) to permit the inflow of ambient air.

The purpose of vent 30 and valve member 33 is to insure that the highly effective sealing action of the periurethral cup against the periurethral floor and vaginal introitus will not interfere with proper flow of urine through discharge tube 14 to reservoir 16. If it were not for the vent, a column of liquid flowing downwardly through the discharge tube would generate a relative negative pressure that might even be sufficient to collapse bellows 13 and/or conduit 14, interfere with the fit of periurethral cup 11, and possibly result in leakage or wearer discomfort. Since vent or port 30 and valve member 33 permit the entry of air at the proximal end of the discharge tube immediately adjacent external pad 12, pressure is equalized and such problems are avoided.

To prevent air which enters the system through the vent from inflating the pouch 16 or other collection device, the pouch may also be provided with air venting means of the type disclosed in U.S. Pat. No. 4,681,572.

Figure 3:
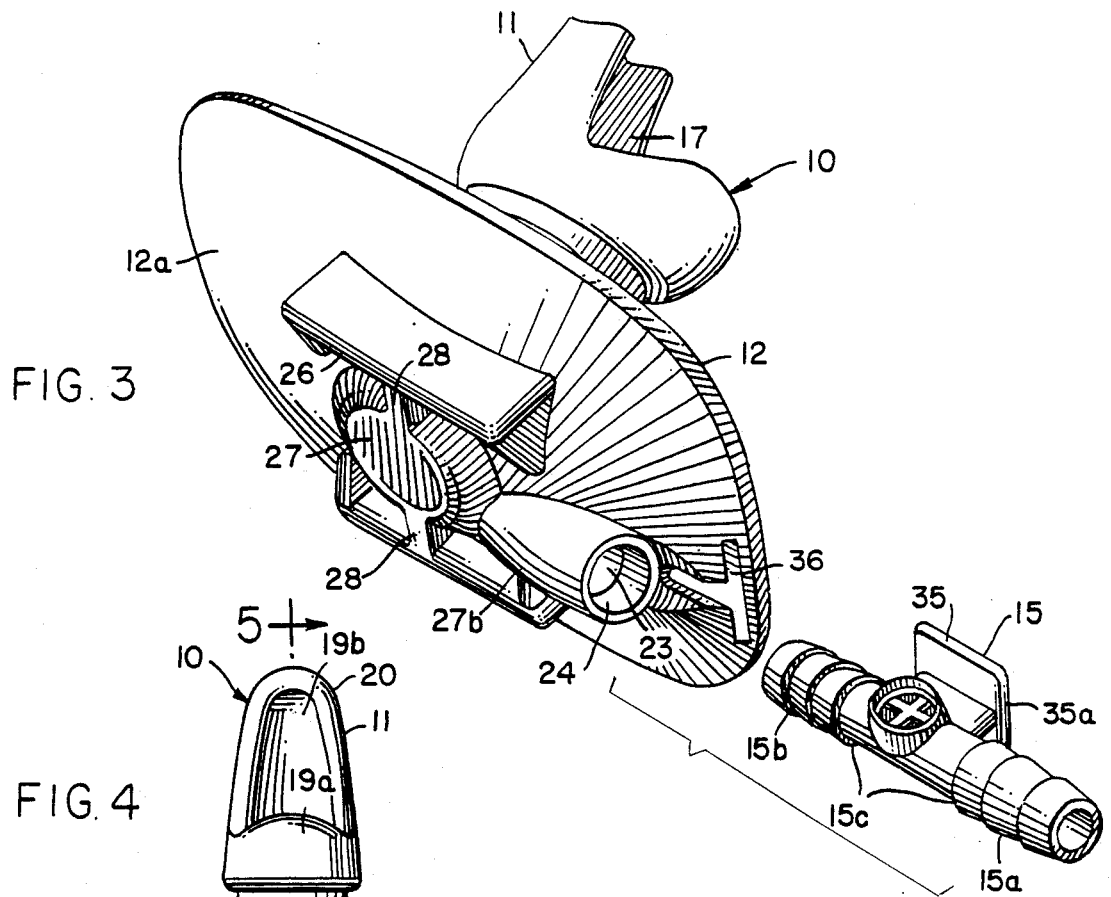
FIG. 3 is a perspective view similar to FIG. 2 but showing the tubular coupling detached from the external pad.
Figure 4:
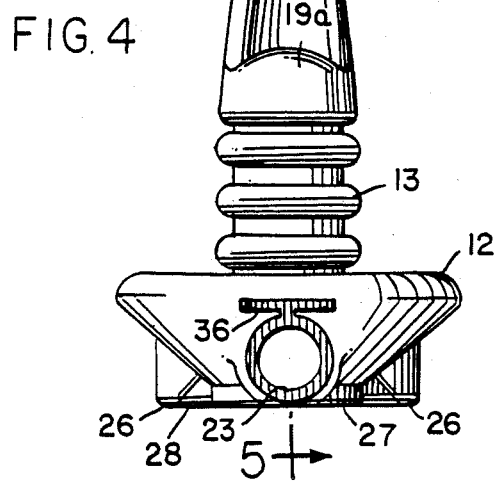
FIG. 4 is a front (anterior) elevational view of the device with the drainage tube and its coupling omitted.

Referring to FIGS. 3, 4, 7, and 8, it will be observed that the tubular coupling 15 has an upstanding projection or rib 35 of T-shaped transverse cross section. The planar horizontal top panel 35a of the rib is rectangular in cross section and, as indicated in FIG. 3, is of substantial lateral and longitudinal extent. When the coupling is joined to pad 12, the T-shaped projection is received within T-shaped slot 36. As a result, coupling 15 and the front (anterior) portion of pad 12 are joined together so that if downward forces are exerted against the distal end of the coupling in normal use of the device (as might occur if a downward force were applied to the flexible discharge tube 14), the coupling 15 will not pull away from the pad. Instead such downward deflecting forces will be resisted by the front portion of the pad or, if not completely resisted, will be accompanied by downward deflection of that portion of the pad. The coupling tube 15 and pad 12 are therefore connected to deflect together and, by acting in concert, unintended disengagement of the parts is prevented or strongly resisted.

While in the foregoing, an embodiment of the invention has been disclosed in considerable detail for purposes of illustration, it will be understood by those skilled in the art that many of these details may be varied without departing from the spirit and scope of the invention.

We claim:

1. A female urinary incontinence device having a periurethral cup of soft, compressible material having an upper opening defined by smoothly-rounded contact surfaces for engaging the periurethral floor and vaginal introitus of a wearer; said cup also having a lower opening; an external pad of soft, flexible, resilient material having an upper surface for externally contacting the labia majora of a wearer; said pad having an inlet in said upper surface and having a generally horizontal discharge passage extending there through along the sagittal midplane thereof; said discharge passage having a first end portion communicating with said inlet and a second end portion terminating in an outlet; a compressible tubular elastic bellows extending between said lower opening of said cup and said inlet of said pad; said pad having an undersurface with laterally-disposed support surface portions; said support surface portions being located on opposite sides of said sagittal midplane and extending below and generally parallel with said discharge passage; said undersurface also including a medial support surface portion disposed between said lateral surface portions and extending towards said outlet.

2. The device of claim 1 in which there are a pair of laterally-disposed support surface portions spaced apart from each other on opposite sides of said sagittal midplane.

3. The device of claim 2 in which said laterally-disposed support surface portions are elongated and parallel with each other.

4. The device of claim 1 in which said lateral and medial support surface portions of said undersurface lie in a common plane.

5. The device of claim 4 in which said bellows has a longitudinal axis extending normal to said common plane of said support surface portions.

6. The device of claim 1 in which said outlet faces anteriorly and said medial surface portion extends anteriorly beyond said lateral support surface portions.

7. The device of claims 1 or 2 in which said upper surface of said pad is concave.

8. The device of claims 1 or 2 in which a discharge tube has one end thereof detachably connected to said pad at said outlet.

9. The device of claim 8 in which said discharge tube includes a relatively rigid tubular coupling at said one end; said coupling having an insert portion received in said outlet.

10. The device of claim 9 in which said coupling includes a laterally-directed vent; and valve means disposed within said vent for permitting gaseous inflow into, but blocking fluid outflow from, said coupling.

11. The device of claim 9 in which means are provided by said pad and said coupling for preventing rotation of said coupling in said outlet and for holding said tubular coupling in longitudinal alignment with said discharge passage.

12. The device of claim 11 in which said means includes a longitudinal projection extending upwardly from said coupling and a slot formed in said pad above said outlet for frictionally receiving said projection.

13. The device of claim 12 in which said projection and said slot are T-shaped in transverse cross section.

14. A female urinary incontinence device having a periurethral cup of soft, compressible material having an upper opening defined by smoothly-rounded contact surfaces for engaging the periurethral floor and vaginal introitus of a wearer; said cup also having a lower opening; an external pad of soft, flexible, resilient material having an upper surface for externally contacting the labia majora of a wearer; said pad having an inlet in said upper surface and having a generally horizontal discharge passage extending there through along the sagittal midplane thereof; said discharge passage having a rear end portion communicating with said inlet and having a front end portion terminating in an outlet; a compressible tubular elastic bellows extending between said lower opening of said cup and said inlet of said pad; and a discharge tube having one end thereof detachably connected to said pad at said outlet; said discharge tube including a relatively rigid tubular coupling at said one end; said coupling having an insert portion received in said outlet; said coupling also including a laterally-directed vent and one-way valve means at said vent for permitting fluid inflow but preventing fluid outflow through said vent.

15. The device of claim 14 in which means are provided by said pad and said coupling for preventing rotation of said coupling in said outlet and for holding said tubular coupling in longitudinal alignment with said discharge passage.

16. The device of claim 15 in which said means for preventing rotation includes a longitudinal projection extending upwardly from said coupling and a slot formed in said pad above said outlet for frictionally receiving said projection.

17. The device of claim 16, in which said projection and said slot are of T-shaped transverse section.

* * * * *